(12) United States Patent
Nikolchev et al.

(10) Patent No.: US 8,066,007 B2
(45) Date of Patent: Nov. 29, 2011

(54) CONTRACEPTIVE TRANSCERVICAL FALLOPIAN TUBE OCCLUSION DEVICES AND THEIR DELIVERY

(75) Inventors: Julian Nikolchev, Portola Valley, CA (US); Dai Ton, San Jose, CA (US); Amy Thurmond, Portland, OR (US)

(73) Assignee: Conceptus, Inc., Mountain View, CA (US)

( * ) Notice: Subject to any disclaimer, the term of this patent is extended or adjusted under 35 U.S.C. 154(b) by 1 day.

(21) Appl. No.: 11/497,468

(22) Filed: Jul. 31, 2006

(65) Prior Publication Data

US 2007/0044808 A1    Mar. 1, 2007

Related U.S. Application Data

(63) Continuation of application No. 10/846,047, filed on May 14, 2004, which is a continuation of application No. 09/591,874, filed on Jun. 12, 2000, now Pat. No. 6,871,650, which is a continuation of application No. 08/474,779, filed on Jun. 7, 1995, now Pat. No. 6,176,240.

(51) Int. Cl.
A61F 6/06 (2006.01)

(52) U.S. Cl. ........................................ 128/830; 128/831

(58) Field of Classification Search ........... 128/830–841
See application file for complete search history.

(56) References Cited

U.S. PATENT DOCUMENTS

| | | |
|---|---|---|
| 2,102,270 A | 12/1937 | Hyams |
| 2,365,296 A | 12/1944 | Schimpf |
| 3,042,030 A | 7/1962 | Read |
| 3,334,629 A | 8/1967 | Cohn |
| 3,404,682 A | 10/1968 | Waldron |
| 3,405,711 A | 10/1968 | Bakunin |
| 3,422,813 A | 1/1969 | Braley et al. |
| 3,463,141 A | 8/1969 | Mozolf |
| 3,467,090 A | 9/1969 | Zollett |
| 3,561,438 A | 2/1971 | Canel |
| 3,563,235 A | 2/1971 | Zipper |
| 3,598,115 A | 8/1971 | Horne, Jr. |
| 3,620,212 A | 11/1971 | Fannon et al. |

(Continued)

FOREIGN PATENT DOCUMENTS

AU    32520/78    7/1979

(Continued)

OTHER PUBLICATIONS

EPO Search Report for European Divisional Patent Application No. 07002727.1, mailed May 30, 2007, total 8 pages.

(Continued)

*Primary Examiner* — Michael A. Brown
(74) *Attorney, Agent, or Firm* — Blakely, Sokoloff, Taylor & Zafman LLP

(57) ABSTRACT

The invention provides intrafallopian devices and non-surgical methods for their placement to prevent conception. The efficacy of the device is enhanced by forming the structure at least in part from copper or a copper alloy. The device is anchored within the fallopian tube by imposing a secondary shape on a resilient structure, the secondary shape having a larger cross-section than the fallopian tube. The resilient structure is restrained in a straight configuration and transcervically inserted within the fallopian tube, where it is released. The resilient structure is then restrained by the walls of the fallopian tube, imposing anchoring forces as it tries to resume the secondary shape.

29 Claims, 4 Drawing Sheets

U.S. PATENT DOCUMENTS

| | | | |
|---|---|---|---|
| 3,675,639 A * | 7/1972 | Cimber | 128/831 |
| 3,675,642 A | 7/1972 | Lord | |
| 3,680,542 A | 8/1972 | Climber | |
| 3,687,129 A | 8/1972 | Nuwavser | |
| 3,722,500 A | 3/1973 | Robinson | |
| 3,760,806 A | 9/1973 | Leeper | |
| 3,763,856 A | 10/1973 | Blomberg | |
| 3,768,102 A | 10/1973 | Kwan-Gett et al. | |
| 3,774,600 A | 11/1973 | Cognat | |
| 3,803,308 A | 4/1974 | Zipper | |
| 3,805,767 A | 4/1974 | Erb | |
| 3,840,016 A | 10/1974 | Lindemann | |
| 3,858,571 A | 1/1975 | Rudolph | |
| 3,858,586 A | 1/1975 | Lessen | |
| 3,868,956 A | 3/1975 | Alfidi et al. | |
| 3,895,634 A | 7/1975 | Berger et al. | |
| 3,918,431 A | 11/1975 | Sinnreich | |
| 3,926,195 A | 12/1975 | Bleier et al. | |
| 3,938,527 A | 2/1976 | Rioux et al. | |
| 3,973,560 A | 8/1976 | Emmett | |
| 3,982,542 A | 9/1976 | Ford et al. | |
| 4,003,380 A | 1/1977 | Wien | |
| RE29,345 E | 8/1977 | Erb | |
| 4,040,417 A | 8/1977 | Zipper | |
| 4,057,063 A | 11/1977 | Gieles et al. | |
| 4,085,743 A | 4/1978 | Yoon | |
| 4,111,196 A | 9/1978 | Emmett | |
| 4,135,495 A | 1/1979 | Borgen | |
| 4,136,695 A | 1/1979 | Dafoe | |
| 4,140,126 A | 2/1979 | Choudhury | |
| 4,143,656 A | 3/1979 | Holmes | |
| 4,158,050 A | 6/1979 | Zipper | |
| 4,160,446 A | 7/1979 | Barrington | |
| 4,181,725 A | 1/1980 | Voorhees et al. | |
| 4,185,618 A | 1/1980 | Corey | |
| 4,207,891 A | 6/1980 | Boldue | |
| 4,245,623 A | 1/1981 | Erb | |
| 4,246,896 A | 1/1981 | Horne, Jr. et al. | |
| 4,326,511 A | 4/1982 | Zimerman | |
| 4,353,363 A | 10/1982 | Sopena Quesada | |
| 4,365,621 A | 12/1982 | Brundin | |
| 4,374,523 A | 2/1983 | Yoon | |
| 4,416,660 A | 11/1983 | Dafoe | |
| 4,478,837 A | 10/1984 | Schenker | |
| 4,485,814 A | 12/1984 | Yoon | |
| 4,503,569 A | 3/1985 | Dotter | |
| 4,509,504 A | 4/1985 | Brundin | |
| 4,523,590 A | 6/1985 | Roth et al. | |
| 4,537,186 A | 8/1985 | Verschoof et al. | |
| 4,572,162 A | 2/1986 | Livesay et al. | |
| 4,574,806 A | 3/1986 | McCarthy | |
| 4,579,110 A | 4/1986 | Hamou | |
| 4,595,000 A | 6/1986 | Hamou | |
| 4,601,698 A | 7/1986 | Moulding, Jr. | |
| 4,606,336 A | 8/1986 | Zeluff | |
| 4,612,924 A | 9/1986 | Cimber | |
| 4,628,924 A | 12/1986 | Cimber | |
| 4,638,803 A | 1/1987 | Rand | |
| 4,655,771 A | 4/1987 | Wallsten | |
| 4,700,701 A | 10/1987 | Montaldi | |
| 4,715,365 A | 12/1987 | Cimber | |
| 4,717,387 A | 1/1988 | Inoue et al. | |
| 4,724,832 A | 2/1988 | Strubel et al. | |
| 4,727,866 A | 3/1988 | Livesay et al. | |
| 4,731,052 A | 3/1988 | Seitz, Jr. | |
| 4,733,665 A | 3/1988 | Palmaz | |
| 4,788,966 A | 12/1988 | Yoon | |
| 4,805,618 A | 2/1989 | Ueda et al. | |
| 4,808,399 A | 2/1989 | Rypacek et al. | |
| 4,821,741 A | 4/1989 | Mohajer | |
| 4,824,434 A | 4/1989 | Seitz, Jr. | |
| 4,846,834 A | 7/1989 | Von Recum et al. | |
| 4,932,421 A | 6/1990 | Kaali et al. | |
| 4,932,422 A | 6/1990 | Ragheb | |
| 4,937,254 A | 6/1990 | Sheffield et al. | |
| 4,943,290 A | 7/1990 | Rexroth et al. | |
| 4,969,458 A | 11/1990 | Wiktor | |
| 4,970,298 A | 11/1990 | Silver et al. | |
| 4,983,177 A | 1/1991 | Wolf | |
| 4,994,069 A * | 2/1991 | Ritchart et al. | 606/191 |
| 5,002,552 A | 3/1991 | Casey | |
| 5,065,751 A | 11/1991 | Wolf | |
| 5,071,407 A | 12/1991 | Termin et al. | |
| 5,095,917 A | 3/1992 | Vancaillie | |
| 5,108,420 A | 4/1992 | Marks | |
| 5,122,136 A | 6/1992 | Guglielmi et al. | |
| 5,122,137 A | 6/1992 | Lennox | |
| 5,133,709 A | 7/1992 | Prince | |
| 5,147,353 A | 9/1992 | Everett et al. | |
| 5,147,370 A | 9/1992 | McNamara et al. | |
| 5,163,958 A | 11/1992 | Pinchuk | |
| 5,176,692 A | 1/1993 | Wilk et al. | |
| 5,192,301 A | 3/1993 | Kamiya et al. | |
| 5,195,964 A | 3/1993 | Kletzky et al. | |
| 5,197,978 A | 3/1993 | Hess | |
| 5,207,684 A | 5/1993 | Nobles | |
| 5,222,964 A | 6/1993 | Cooper | |
| 5,226,911 A | 7/1993 | Chee et al. | |
| 5,234,437 A | 8/1993 | Sepetka | |
| 5,250,071 A | 10/1993 | Palermo | |
| 5,254,132 A * | 10/1993 | Barley et al. | 606/214 |
| 5,259,836 A | 11/1993 | Thurmond et al. | |
| 5,261,916 A | 11/1993 | Engleson | |
| 5,303,719 A | 4/1994 | Wilk et al. | |
| 5,304,194 A | 4/1994 | Chee et al. | |
| 5,304,195 A | 4/1994 | Twyford, Jr. et al. | |
| 5,304,228 A | 4/1994 | Prince | |
| 5,312,415 A | 5/1994 | Palermo | |
| 5,330,483 A | 7/1994 | Heaven et al. | |
| 5,342,348 A | 8/1994 | Kaplan | |
| 5,346,498 A | 9/1994 | Greelis et al. | |
| 5,350,397 A | 9/1994 | Palermo et al. | |
| 5,354,295 A | 10/1994 | Guglielmi et al. | |
| 5,354,309 A | 10/1994 | Schnepp-Pesch et al. | |
| 5,356,388 A | 10/1994 | Sepetka et al. | |
| 5,364,393 A | 11/1994 | Auth et al. | |
| 5,366,472 A | 11/1994 | Hillstead | |
| 5,377,668 A | 1/1995 | Ehmsen et al. | |
| 5,382,259 A * | 1/1995 | Phelps et al. | 606/151 |
| 5,382,260 A | 1/1995 | Dormandy et al. | |
| 5,382,261 A | 1/1995 | Palmaz | |
| 5,389,089 A | 2/1995 | Bauer et al. | |
| 5,389,100 A | 2/1995 | Bacich et al. | |
| 5,411,549 A | 5/1995 | Peters | |
| 5,423,829 A | 6/1995 | Pham et al. | |
| 5,423,849 A | 6/1995 | Engelson et al. | |
| 5,433,708 A * | 7/1995 | Nichols et al. | 604/113 |
| 5,443,500 A | 8/1995 | Sigwart | |
| 5,458,636 A | 10/1995 | Brancato | |
| 5,469,867 A | 11/1995 | Schmitt | |
| 5,474,089 A | 12/1995 | Waynant | |
| 5,499,995 A | 3/1996 | Teirstein | |
| 5,507,768 A | 4/1996 | Lau et al. | |
| 5,514,176 A | 5/1996 | Bosley, Jr. | |
| 5,522,822 A | 6/1996 | Phelps et al. | |
| 5,522,836 A | 6/1996 | Palermo | |
| 5,534,007 A | 7/1996 | St. Germain et al. | |
| 5,545,210 A | 8/1996 | Hess et al. | |
| 5,549,624 A | 8/1996 | Mirigian et al. | |
| 5,555,896 A | 9/1996 | Cimber | |
| 5,556,396 A | 9/1996 | Cohen et al. | |
| 5,562,641 A | 10/1996 | Flomenblit et al. | |
| 5,562,654 A | 10/1996 | Smith | |
| 5,569,245 A | 10/1996 | Guglielmi et al. | |
| 5,578,074 A | 11/1996 | Mirigian | |
| 5,582,619 A | 12/1996 | Ken | |
| 5,601,593 A | 2/1997 | Freitag | |
| 5,601,600 A | 2/1997 | Ton | |
| 5,624,449 A | 4/1997 | Pham et al. | |
| 5,624,461 A | 4/1997 | Mariant | |
| 5,630,797 A | 5/1997 | Diedrich et al. | |
| 5,634,877 A | 6/1997 | Salama | |
| 5,656,036 A | 8/1997 | Palmaz | |
| 5,662,712 A | 9/1997 | Pathak et al. | |
| 5,690,666 A | 11/1997 | Berenstein et al. | |
| 5,690,842 A | 11/1997 | Panchinson | |
| 5,718,711 A | 2/1998 | Berenstein et al. | |

| | | | | | |
|---|---|---|---|---|---|
| 5,725,777 A | 3/1998 | Taylor | DE | 2537620 A1 | 2/1977 |
| 5,743,905 A | 4/1998 | Eder et al. | DE | 2635863 A1 | 2/1977 |
| 5,746,692 A | 5/1998 | Bacich et al. | DE | 2803685 A1 | 1/1978 |
| 5,746,769 A | 5/1998 | Ton et al. | DE | 2803685 A1 | 8/1979 |
| 5,749,915 A | 5/1998 | Slepian | DE | 2913036 A1 | 10/1980 |
| 5,755,773 A | 5/1998 | Evans et al. | EP | 0010812 A1 | 10/1979 |
| 5,766,160 A | 6/1998 | Samson et al. | EP | 0010812 B1 | 5/1980 |
| 5,766,203 A | 6/1998 | Imran et al. | EP | 105669 B1 | 9/1983 |
| 5,772,669 A | 6/1998 | Vrba | EP | 183372 A1 | 10/1985 |
| 5,795,288 A | 8/1998 | Cohen et al. | EP | 241971 B1 | 3/1987 |
| 5,807,236 A | 9/1998 | Bacich et al. | EP | 421966 A1 | 9/1990 |
| 5,843,158 A | 12/1998 | Lenker et al. | EP | 0541258 A1 | 5/1993 |
| 5,876,398 A | 3/1999 | Mulier et al. | EP | 0686382 A1 | 12/1995 |
| 5,885,601 A | 3/1999 | Sokal | EP | 0739608 | 10/1996 |
| 5,895,749 A | 4/1999 | Alvarez | EP | 0891757 A2 | 1/1999 |
| 5,897,551 A | 4/1999 | Everett et al. | GB | 1460077 | 12/1976 |
| 5,925,059 A | 7/1999 | Palermo et al. | GB | 1530565 | 11/1978 |
| 5,935,137 A | 8/1999 | Saadat | GB | 2010728 A | 7/1979 |
| 5,954,715 A | 9/1999 | Harrington et al. | GB | 2038186 A | 7/1980 |
| 5,968,052 A | 10/1999 | Sullivan, III et al. | GB | 2150439 A | 7/1985 |
| 5,976,162 A | 11/1999 | Doan | GB | 2211095 A | 6/1989 |
| 5,979,446 A | 11/1999 | Loy | JP | 1-113045 | 5/1989 |
| 6,019,757 A | 2/2000 | Scheldrup | JP | 5-269197 | 10/1993 |
| 6,042,590 A | 3/2000 | Sporri et al. | NL | 7810696 | 4/1980 |
| 6,066,139 A | 5/2000 | Ryan et al. | WO | WO 80/02369 | 11/1980 |
| 6,068,626 A | 5/2000 | Harrington et al. | WO | WO 83/00011 | 1/1983 |
| 6,080,152 A | 6/2000 | Nardella et al. | WO | WO 8809648 A1 | 12/1988 |
| 6,096,052 A | 8/2000 | Callister et al. | WO | WO 93/06884 A1 | 4/1993 |
| 6,143,007 A | 11/2000 | Mariant | WO | WO94/06503 A1 | 3/1994 |
| 6,145,505 A | 11/2000 | Nikolchev | WO | WO 94/07560 | 4/1994 |
| 6,156,742 A | 12/2000 | Mackenzie | WO | WO 94/10936 A1 | 5/1994 |
| 6,164,280 A | 12/2000 | Everett et al. | WO | WO 94/11051 A1 | 5/1994 |
| 6,176,240 B1 | 1/2001 | Nikolchev et al. | WO | WO 94/24944 A1 | 11/1994 |
| 6,178,354 B1 | 1/2001 | Gibson | WO | WO 94/26175 | 11/1994 |
| 6,187,027 B1 | 2/2001 | Mariant et al. | WO | WO 95/01123 | 1/1995 |
| 6,270,495 B1 | 8/2001 | Palermo | WO | WO 95/25490 A1 | 9/1995 |
| 6,286,510 B1 | 9/2001 | Ray et al. | WO | WO 96/22122 A1 | 7/1996 |
| 6,309,384 B1 | 10/2001 | Harrington et al. | WO | WO 96/40023 | 12/1996 |
| 6,346,102 B1 | 2/2002 | Harrington et al. | WO | WO 96/40024 | 12/1996 |
| 6,357,443 B1 | 3/2002 | Loy | WO | WO 96/40024 A1 | 12/1996 |
| 6,371,118 B1 | 4/2002 | Ray et al. | WO | WO 97/08997 | 3/1997 |
| 6,401,719 B1 | 6/2002 | Farley et al. | WO | WO 97/12569 A1 | 4/1997 |
| 6,432,116 B1 | 8/2002 | Callister et al. | WO | WO 97/13451 | 4/1997 |
| 6,513,528 B2 | 2/2003 | Burton et al. | WO | WO 97/27893 | 8/1997 |
| 6,526,979 B1 | 3/2003 | Nikolchev et al. | WO | WO 97/46175 A1 | 12/1997 |
| 6,550,480 B2 | 4/2003 | Feldman et al. | WO | WO 97/49345 A1 | 12/1997 |
| 6,599,299 B2 | 7/2003 | Schultz | WO | WO 98/26737 A1 | 6/1998 |
| 6,679,266 B2 | 1/2004 | Nikolchev et al. | WO | WO 98/31308 A1 | 7/1998 |
| 6,705,323 B1 | 3/2004 | Nikolchev et al. | WO | WO 98/55046 A1 | 12/1998 |
| 6,712,810 B2 | 3/2004 | Harrington et al. | WO | WO 99/15116 | 4/1999 |
| 6,726,682 B2 | 4/2004 | Harrington et al. | WO | WO 00/44323 A1 | 8/2000 |
| 6,758,831 B2 | 7/2004 | Ryan | WO | WO 0137760 A2 | 5/2001 |
| 6,780,182 B2 | 8/2004 | Bowman et al. | WO | WO 03/088879 | 10/2004 |
| 6,802,825 B2 | 10/2004 | Ackerman et al. | WO | WO 2004/098469 | 11/2004 |
| 7,073,504 B2 | 7/2006 | Callister et al. | | | |
| 2001/0016738 A1 | 8/2001 | Harrington et al. | | | |
| 2001/0041900 A1 | 11/2001 | Callister et al. | | | |
| 2002/0013589 A1 | 1/2002 | Callister et al. | | | |
| 2002/0072744 A1 | 6/2002 | Harrington et al. | | | |
| 2003/0015203 A1 | 1/2003 | Makower et al. | | | |
| 2003/0029457 A1 | 2/2003 | Callister et al. | | | |
| 2003/0051735 A1 | 3/2003 | Pavcnik et al. | | | |
| 2003/0199913 A1 | 10/2003 | Dubrul et al. | | | |
| 2003/0220636 A1 | 11/2003 | Bowman et al. | | | |
| 2004/0172051 A1 | 9/2004 | Ravikumar | | | |
| 2004/0202694 A1 | 10/2004 | Burbank et al. | | | |
| 2004/0204720 A1 | 10/2004 | Harrington et al. | | | |
| 2004/0220585 A1 | 11/2004 | Nikolchev | | | |
| 2004/0255958 A1 | 12/2004 | Harrington et al. | | | |
| 2005/0033281 A1 | 2/2005 | Bowman et al. | | | |
| 2005/0045183 A1 | 3/2005 | Callister et al. | | | |
| 2005/0192616 A1 | 9/2005 | Callister et al. | | | |
| 2005/0217680 A1 | 10/2005 | Callister et al. | | | |

FOREIGN PATENT DOCUMENTS

| | | |
|---|---|---|
| CN | 1047447 A | 12/1990 |
| CN | 1073088 A | 6/1993 |
| DE | 2404605 A1 | 8/1975 |
| DE | 2525650 A1 | 12/1976 |

OTHER PUBLICATIONS

PCT Notification of Transmittal of the International Search Report or the Declaration PCT/US96/07483 dated Sep. 5, 1996, 5 pages.

PCT Written Opinion PCT/US96/07486 dated May 19, 1997, 4 pages.

PCT Notification of Transmittal of the International Preliminary Examination Report, PCT/US96/07486 dated Sep. 8, 1997.

PCT Written Opinion, PCT/US98/20031 dated Aug. 31, 1999, 4 pages.

PCT Notification of Transmittal of the International Search Report, PCT/US98/20031 dated Jan. 20, 1999, 5 pages.

PCT Notification of Transmittal of International Preliminary Examination Report, PCT/US98/20031 dated Jun. 30, 2000, 5 pages.

Vancaillie, et al, "A New Method of Transcervical Female Sterilization: Preliminary Results in Rabbits," Fertility and Sterility vol. 51, No. 2, Feb. 1989, pp. 335-338.

Brueschke, E.E. et al., "Transcervical tubal occlusion with a steerable hysteroscope: Implantation of devices into extirpated human uteri," Am. J. Obstet. Gynecol., vol. 127, No. 2; pp. 118-124, 1977.

Brundin, J.,"Transcervical sterilization in the human female by hysteroscopic application of hydrogelic occlusive devices into the intramural parts of the Fallopian tubes: 10 years experience of the P-block," *European Journal of Obstetrics & Gynecology and Reproductive Biology*, vol. 39, pp. 41-49, 1991.
Complete Chinese-to English translation of Chinese Patent Publication No. CN 1047447A.
Conceptus Annual Report (1995) pp. 3,5,7,9,13-14 and 22.
Conceptus Annual Report (1996) pp. x,3,9,and 13-14.
Erb, R.A. et al., "Hysteroscopic Oviduct Blocking with Formed-in-Place Silicone Rubber Plugs," *The Journal of Reproductive Medicine*, pp. 65-68, Aug. 1979.
Gordon, A.G., et al., *Atlas of Gynecologic Endoscopy*, Mosby-Wolfe Press, 2$^{nd}$ Edition, 1995 (Title Page and Table of Contents are enclosed herewith).
Gupta, D.N. et al., "Antifertility Effect of an Intrafallopian Tubal Copper Device," *Indian J. Exp. Biol.*, vol. 14, pp. 316-319, May 1976.
Hamou, J. et al., "Hysteroscopic Reversible Tubal Sterilization," *ACTA Europaea Fertilitatis*, vol. 15, No. 2, 1984.
Reed, T.P. et al., "Tubal Occlusion with Silicone Rubber," *The Journal of Reproductive Medicine*, pp. 25-28, Jul. 1980.
Ross, P.L. et al., "Transcatheter Tubal Sterilization in Rabbits," *Investigative Radiology*, vol. 29, No. 5, pp. 570-573, 1994.
Sciarra, J.J., et al., eds., *Advances in Female Sterilization Techniques*, Harper & Row, Publishers, 1976, Title page and Table of Contents are enclosed herewith, pp. 169-181, 186-189.
Steptoe, P.C., "Potential Use of Intratubal Stents for Reversible Sterilization," *Laaroscopy*, pp. 91-99, circa 1976.
Brueschkle, et al., "A Steerable Hysteroscopic and Mechanical Tubal Occlusive Devices", *Advances in Female Sterilization Techniques*, Sciarra, et al., Eds., Harper & Row, Publishers, 1976, pp. 182-198.
Cooper, "Hysteroscopic Sterilization", *Fertility Control*, 1985, Corson, et al., Eds., Little, Brown & Co. Boston, First Edition, pp. 119-131.
Request for Interference with U.S. Patent No. 6,096,052 under 37 CFR§ 1.607 and Second Preliminary Amendment, filed on Oct. 3, 2001 with US Patent Office.
Corfman, "An Instrument for Transcervical Treatment of the Oviducts and Uterine Comua", *Obstetrics and Gynecology*, 1996, 27(6):880-884.
Darabi, et al., "Collaborative Study on Hysteroscopic Sterilization Procedures: Final Report", *Risks, Benefits, and Controversies in Fertility Control*, 1978, Sciarra, et al., Eds., Harper & Row, New York, pp. 81-101.
Hosseintan, et al., "Hysteroscopic Implantation of Uterotubal Junction Blocking Devices", *Advances in Female Sterilization Techniques*, 1976, Sciarra, et al., Eds., Harper & Row, New York, pp. 169-175.
Quinones et al., "Hysteroscopic Sterilization", *Int. J. Gynecol. Obstet.*, 1976, 14:27-34.
Richart et al., "Evaluation of Polymer Flock and Metal Alloy Intra-Tubal Device in Pigtail Monkeys", *Contraception*, 1978, 18(5):459-468.
Sciarra, "Heteroscopic Approaches for Tubal Closure", *Research Frontiers in Fertility Regulation*, 1980, Zatuchni, et al., Eds. Harper & Row, New York, pp. 270-286.
Conceptus, Inc.'s *Complaint for Declaratory Judgment of Patent Non-Infringement, Invalidity and Unenforceability; and Demand for Jury Trial*, Case #:3:02-cv-1968), filed in U.S. District Court Northern District of California, San Francisco Division, executed Apr. 22, 2002, pp. 1-10.
Conceptus, Inc.'s *Conceptus, Inc.'s Patent Local Rule 4-2 Preliminary Claim Constructions and Extrinsic Evidence, with Proof of Service* Case No. C-02-1968 (MHP), filed in U.S. District Court Northern District of California, San Francisco Division, executed Jun. 19, 2003, pp. 1-16.
Conceptus, Inc.'s *Conceptus' Amended Answer to Ovion's Complaint, Affirmative Defenses and Counterclaims, and Jury Demand*, Case No. C-02-3884 (MHP), filed in U.S. District Court Northern District of California, executed Sep. 26, 2002, pp. 1-12; Proof of Service, pp. 1-2.
Conceptus, Inc.'s *Conceptus' Answer to Ovion's Complaint, Affirmative Defenses and Counterclaims*, Case No. C-02-3884 (MHP), filed in U.S. District Court Northern District of California, executed Sep. 25, 2002, pp. 1-12.
Conceptus, Inc.'s *Conceptus' Motion for Summary Judgment of Invalidity of the Asserted '116 Patent Claims in view of Conceptus, Inc.'s '979* Patent Case No. C-02-1968 (MHP), filed in U.S. District Court Northern District of California, executed Oct. 6, 2003, pp. i-v and 1-25.
Conceptus, Inc.'s *Declaration of Dr. Ralph M. Richart in Support of Conceptus, Inc.'s Motion for Summary Judgment of Invalidity of the Asserted '116 Patent Claims in View of Conceptus, Inc.'s '979* Patent, Case No. C-02-1968 (MHP), filed in U.S. District Court Northern District of California, San Francisco Division, executed Oct. 6, 2003, pp. 1-14, Exhibits 1-5.
Conceptus, Inc.'s *First Amended Complaint for (1) Declaration Judgment of Patent Non-Infringement, Invalidity and Unenforceability; (2) False Advertising Under 15 U.S.C. §1125(A); (3) Trade Libel; (4) Unfair Competition Under Common Law and Cal. B&P §17200 Et Seq.; (5) Unjust Enrichment; and (6) Constructive Trust Demand for Jury Trial*, Case #:3:02-cv-1968 MHP, filed in U.S. District Court Northern District of California, executed Jun. 13, 2001, pp. 1-19.
Conceptus, Inc.'s *Preliminary Invalidity Contentions*, Case #:3:02-cv-1968 MHP and Case No. C-02-3884 (MHP), filed in U.S. District Court Northern District of California San Francisco Division, executed Apr. 20, 2003, pp. 1-129; Certificate of Service, pp. 1-3.
Kerin, J.F., "New Methods for Transcervical Cannulation of the Fallopian Tube," *International Journal of Gynecology and Obstetrics*, 51 Suppl. 1 (1995) pp. S29-S39.
Ovion, Inc.'s and Conceptus, Inc.'s, *Joint Claim Construction and Prehearing Statement Pursuant to Patent Local Rule 4-3*, Case No. C-02-3884 (MHP), filed in U.S. District Court Northern District of California, San Francisco Division, executed Aug. 6, 2003, pp. 1-5; Table 1, pp. 1; Table 2, pp. 1-67; Table 3, pp. 1-6; and *Joint Claim Construction and Prehearing Statement Pursuant to Patent Local Rule 4-3*, with Expert Reports, tabs 1-4 as exhibits.
Ovion, Inc.'s *Complaint for Patent Infringement; and Demand for Jury Trial*, Case No. C-02-3884, filed in U.S. District Court Northern District of California, executed Aug. 13, 2002, pp. 1-5.
Risquez, F., et al., "Transcervical Tubal Cannulation, Past, Present, and Future" *Fertility and Sterilization*, Centro Medico Docente La Trinidad, Caracas, Venezuela, and Mount Sinai Hospital Medical Center and Rush Medical College, Chicago, IL, vol. 60, No. 2, Aug. 1993 pp. 211-226.
Wilson, E.W., "The Evolution and Methods for Female Sterilization", *International Journal of Gynecology & Obstetrics* 51 Suppl. 1 (1995) S2-S13.
Wilson, E.W., "Sterilization" *Baillière's Clinical Obstetrics and Gynecology*, vol. 10, No. 1, Apr. 1996, pp. 103-119.
U.S. District Court California Northern District Civil Docket for Case #:3:02-cv-01968 MHP, pp. 1-10.
U.S. District Court California Northern District Civil Docket for Case #:3:02-cv-03884, pp. 1-8.
Ovion's, Inc.'s *Ovion's Reply to Amended Counterclaims of Conceptus; Demand for Jury Trial*, Case No. -02-3884, filed in U.S. District Court Northern District of California, executed Oct. 25, 2002; with Proof of Service, pp. 1-12.
PCT Notification of Transmittal of the International Search Report or the Declaration PCT/US96/07486 dated Sep. 5, 1996, 4 pages.
PCT Written Opinion PCT/US96/07483 dated Jul. 20, 1997, 4 pages.
Brueschke, Erich E., "Reversible Occlusive Devices," J. Reproductive Medicine for the Obstetrician and Gynecologist, vol. 17, No. 2 (Aug. 1976).
Brundin J., "Ch. 31: Hydrogel Tubal Blocking Device: P-Block," Female Transcervical Sterilization (Gerald Zatuchni, M.D. et al., eds., Harper & Row 1983).
Brundin, J., "Hysteroscopy for Sterilization," Contraceptive Delivery Systems: An International Journal (1982).
Brundin, J., "Observations on the mode of action of an intratubal device, the P-block," Am. J. of Obst. & Gyn., (1987).
Fischer, Michael E. et al., "Silicone Devices for Tubal Occlusion: Radiographic Description and Evaluation," Radiology (Jun. 1984).
Free, Michael J. et al., "Technology for Mechanical Fallopian Tube-Blocking Device," Advances in Female Sterilization Techniques (Harper & Row 1976).

Hamou, J. et al., "Hysteroscopic Placement of Nylon Intratubal Devices for Potentially Reversible Sterilization," The Fallopian Tube: Basic Studies and Clinical Contributions (1986).

Hayashi, Motoyuki, "Ch. 28: Tubal Sterilization by Cornual Coagulation Under Hysteroscopy," Human Sterilization (Ralph Richart et al., eds. 1972).

Hosseinian, Abdol "31: Hysteroscopically Delivered Tubal Plugs," Reversal of Sterilization (John Sciarra et al., eds. Harper & Row 1978).

J.F. Huka & K.F. Omran, "Ch. 27: Cauterization for Tubal Sterilization," Human Sterilization (Ralph Richart et al., eds. 1972).

Jay Cooper & Richard Houck, "Ch. 33: Study Protocol, Criteria, and Complications of the Silicone Plug Procedure," Female Transcervical Sterilization (Gerald Zatuchni, M.D. et al., eds., Harper & Row 1983).

Jay M. Cooper, "Hysteroscopic Sterilization," Clinical Obstetrics and Gynecology, vol. 35, No. 2 (Jun. 1992).

Leonard, Fred "Ch. 14: Polymer Implants," Female Sterilization (Ralph Richart et al., eds. 1972).

Luukkainen, Tapani et al., "15: Five Years' Experience with the Nova-T and T-Cu IUDs," Intrauterine Contraception (Gerald Zatuchni et al., 1984).

Malinak, Russell, M.D. et al., "Oviduct Occlusion Following Implanation of Proplast," Advances in Female Sterilization Techniques (John Sciarra et al., eds. Harper & Row 1976).

Manganiello, Paul D. et. al., "A Bipolar Radiofrequency Catheter Fails to Occlude a Feline Uterine Horn: A Model for Fallopian Tube Occlusion," The Journal of the American Association of Gynecologic Laparoscopists, vol. 5, No. 3 (Aug. 1998).

Medical News, "Hysteroscope simplifies sterilization," J. of Am. Med. Assn., vol. 225, No. 6 (Aug. 6, 1973).

Neuwirth, Robert S. et al., "Hyesteroscopic Sterilization," Hysteroscopic Sterilization (John Sciarra et al. eds., 1974).

Quinones, Rodolfo et al., "Tubal Electrocoagulation Under Hysteroscopic Control," Hysteroscopic Sterilization (John Sciarra et al., eds. 1973).

Richard Houck & Jay Cooper, "Hysteroscopic Tubal Occlusion With Formed-InPlace Silicone Plugs: A Clinical Review," Obst. & Gyn., vol. 62, No. 5 (Nov. 1983).

Robert Neuwirth, Richard Levine, and Ralph Richart, "Hysteroscopic tubal sterilization," Am. J. of Obst. and Gyn., vol. 116, No. 1 (May 1, 1973).

Schmitz-Rode, Thomas et. al., "Experimental Nonsurgical Female Sterilization: Transcervical Implantation of Microspindles in Fallopian Tubes," Journal of Vascular and Interventional Radiology, vol. 5, No. 6 (Nov.-Dec. 1994).

Sciarra, John "26: Hysteroscopic Approaches for Tubal Closure," Fertility and Sterility: Official J of the Am. Fertility Soc., vol. 34, No. 5 & 6 (1980).

Sonmez et al., "Sterilization with fibrin sealant in a rabbit uterine horn model," Am J Obstet Gynecol., vol. 177, issue 3, 1997, pp. 573-578.

Sugimoto, Osamu, "Hysteroscopic Sterilization by Electrocoagulation," Hysteroscopic Sterilization (John Sciarra et al., eds., 1973.

Swope, C.H. "Ch. 23: Production of Clinically Useful Interactions of Laser Radiation With Tissue," Human Sterilization (Ralph Richart et al., eds. 1972).

Theodore Reed & Robert Erb, "Hysteroscopic Tubal Occlusion With Silicone Rubber," Obst. & Gyn., vol. 61, No. 3 (1983).

Thompson, Horace et al., "Evaluation of Experimental Methods of Occluding the Uterotubal Junction," Female Sterilization: Prognosis for Simplified Outpatient Procedures (Gordon Duncan et al, eds. 1972).

U.S. District Court California Northern District, Case #09-cv-02280 WHA, Hologic Inc.'s First Amended Invalidity Contentions, Jan. 22, 2010, 31 pages.

U.S. District Court California Northern District, Case #09-cv-02280 WHA, Hologic Inc.'s Invalidity Contentions, Jan. 4, 2010, 70 pages.

V. Rimkus & K. Semm, "Hysteroscopic Sterilization—a Routine Method?" Int'l. J. Fertility vol. 22 (1977).

Zipper, J. et al., "Supression of fertility by intrauterine copper and zine in rabbits," Am. J. of Obstetrics and Gynecology (Oct. 15, 1969).

Conceptus Office Action for U.S. Appl. No. 11/711,444 mailed Jan. 20, 2011.

Conceptus Office Action for U.S. Appl. No. 11/711,444 mailed Jun. 23, 2011.

* cited by examiner

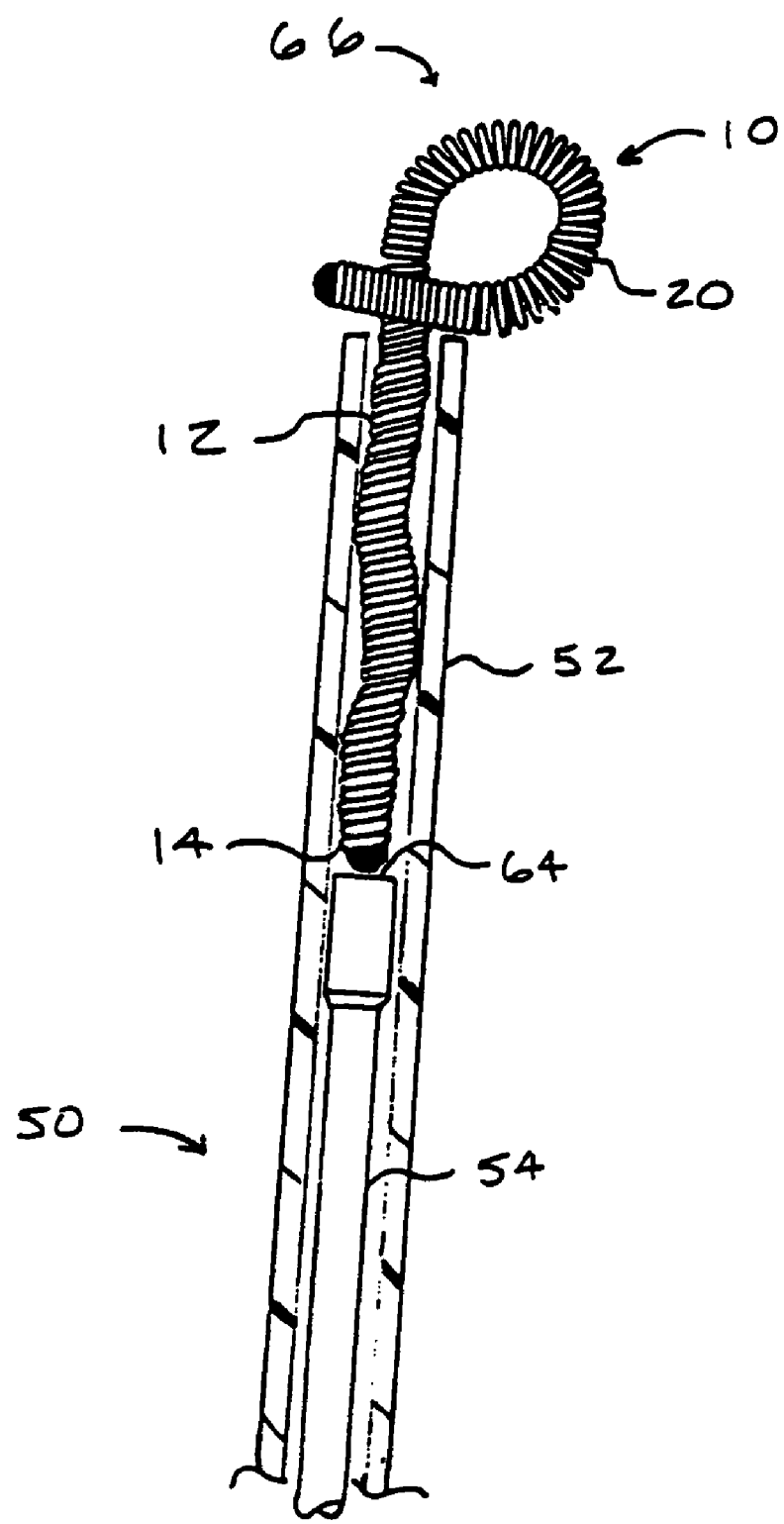
FIG_4

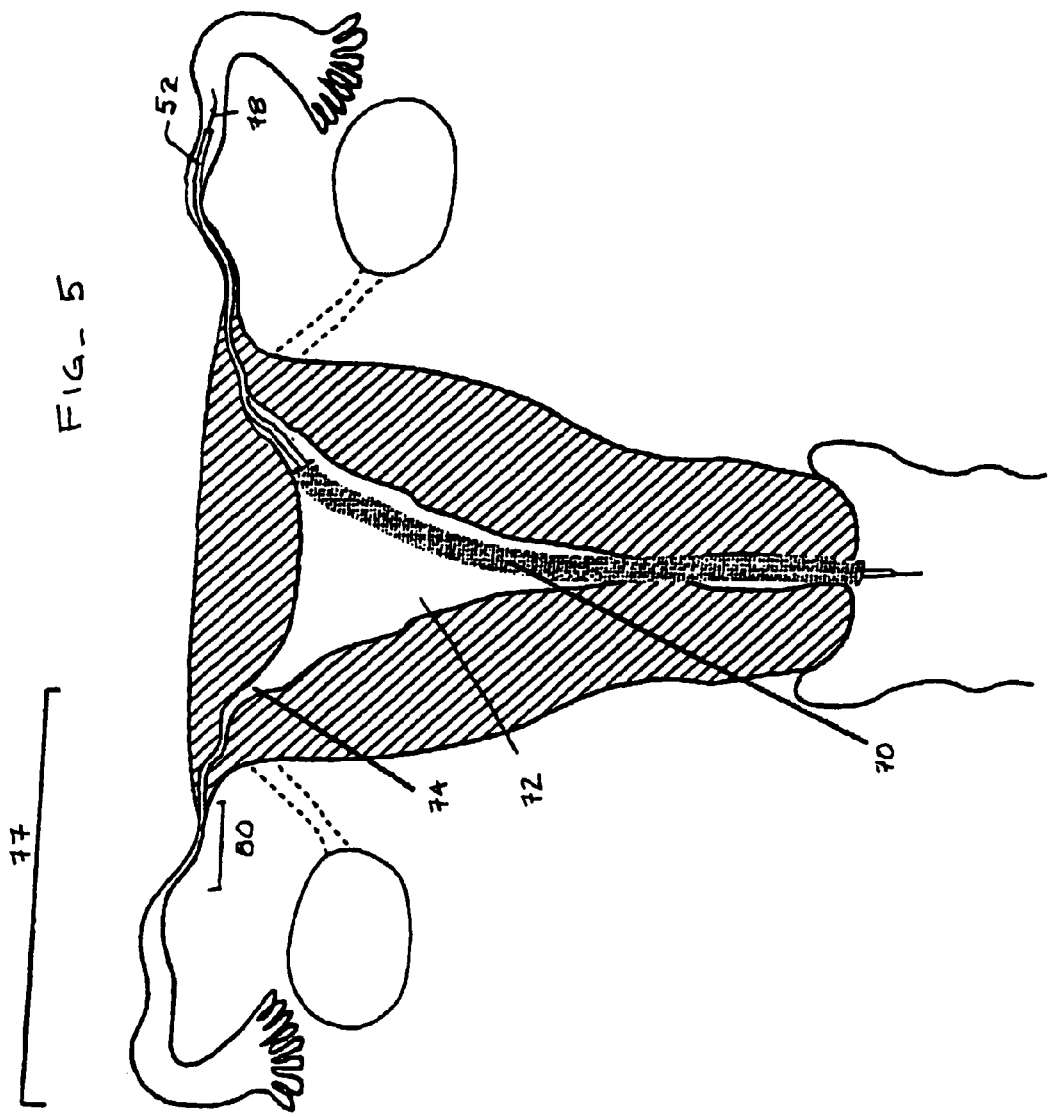
FIG_5

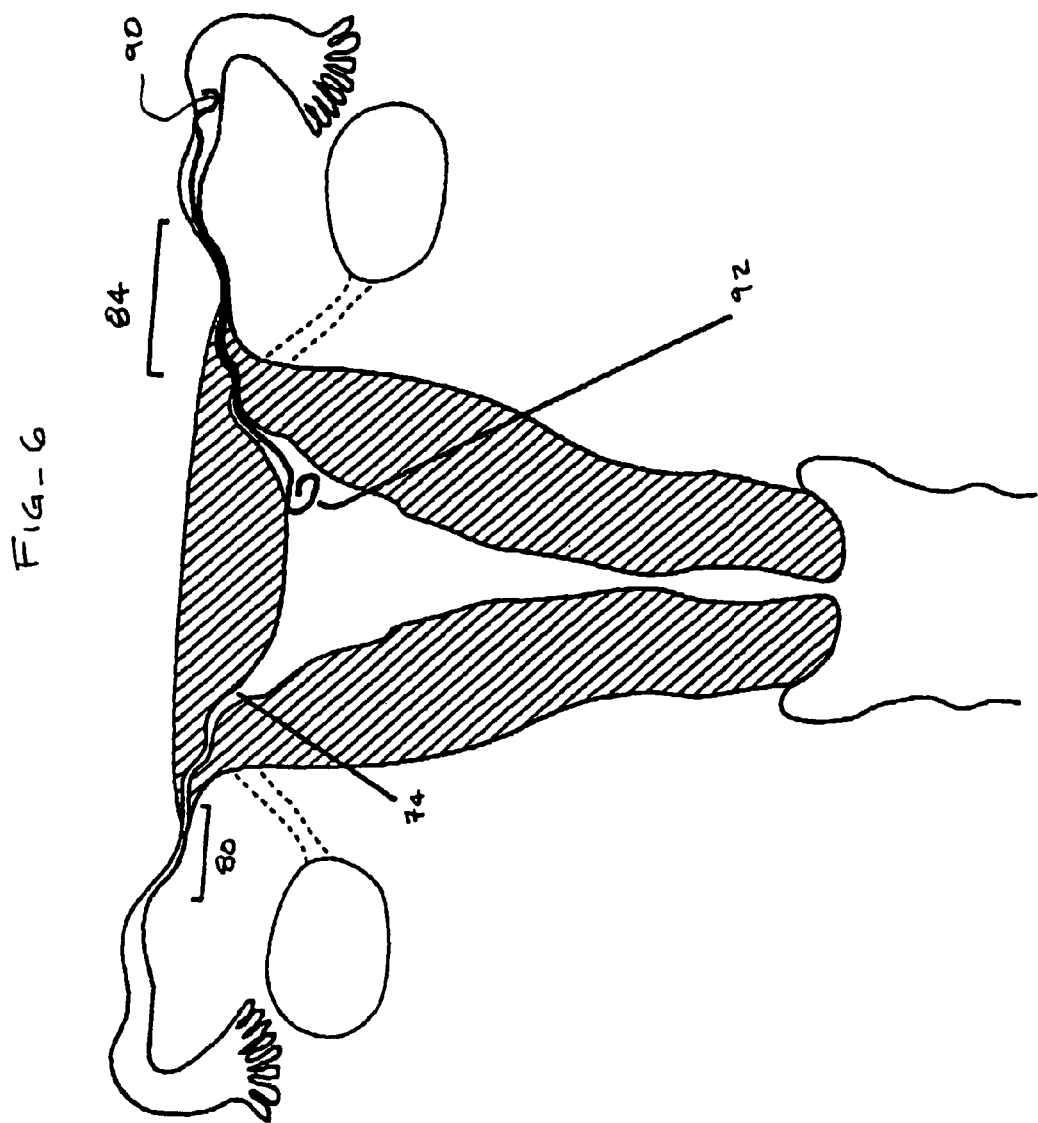

CONTRACEPTIVE TRANSCERVICAL FALLOPIAN TUBE OCCLUSION DEVICES AND THEIR DELIVERY

This application is a continuation of U.S. patent application Ser. No. 10/846,047, filed May 14, 2004, which is a continuation of U.S. patent application Ser. No. 09/591,874, filed Jun. 12, 2000, now U.S. Pat. No. 6,871,650, entitled "Contraceptive Transcervical Fallopian Tube Occlusion Devices and Their Delivery", which is a continuation of U.S. patent application Ser. No. 08/474,779, filed Jun. 7, 1995, now U.S. Pat. No. 6,176,240, entitled "Contraceptive Transcervical Fallopian Tube Occlusion Devices and Their Delivery".

FIELD OF THE INVENTION

The present invention relates generally to contraception, and more particularly to intrafallopian contraceptive devices and nonsurgical methods for their delivery.

Worldwide demand exists for safe, effective methods of both contraception and permanent sterilization. Although a variety of contraception and sterilization methods are available, all of the existing methods have limitations and disadvantages. Thus, the need for additional safe, low cost, reliable methods of contraception and permanent sterilization, both in developed and less developed countries, is widely recognized.

Many presently available contraception methods require significant user involvement, and user non-compliance results in quite high rates of failure. While the theoretical effectiveness of existing contraceptives, including barrier methods and hormonal therapies, is well established, overcoming user noncompliance to improve overall efficacy has proven difficult.

One form of contraception which is less susceptible to user noncompliance is the intrauterine device (IUD). IUDs have been found to have higher rates of reliability, and are effective for a longer period of time, than most other commercially available contraceptives. Unfortunately, IUDs are also associated with serious infectious complications. For this reason, the use of IUDs within the United States has decreased dramatically. Additionally, IUDs are subject to unplanned expulsion, and must be removed due to excessive pain or bleeding in a percentage of cases, further reducing the acceptance of the IUD as a contraceptive method. Interestingly, the efficacy of copper IUDs appears to be higher than that of non-metallic IUDs. The reason for this has not been fully explained.

Commercially available options for permanent sterilization include fallopian tube ligation and vasectomy. These methods are surgical, are difficult to reverse, and are not available to many people in the world. It is common knowledge that fertilization occurs in the fallopian tubes where the sperm and ovum meet. Tubal ligation avoids this by complete occlusion of the fallopian tubes.

It has previously been proposed to reversibly occlude the fallopian tubes, for example, by in vitro formation of an elastomeric plug, or otherwise anchoring a device on either side of the narrowest region of fallopian tube, called the "isthmus." Such fallopian tube occlusion methods appear promising; however, an unacceptably high percentage of the non-surgical devices proposed to date have become dislodged during previous studies. Even where non-surgical intrafallopian devices have remained in place, they have been found to be only moderately effective at preventing conception.

For these reasons, it would be desirable to provide effective, reliable intrafallopian devices for contraception and sterilization. It would be particularly desirable to provide highly effective intrafallopian devices which did not require surgery for placement. It would be especially desirable if such devices and methods allowed easy placement of the device, but were less susceptible to being dislodged than previously proposed non-surgical intrafallopian devices.

DESCRIPTION OF THE RELATED ART

The experimental use of a stainless steel intrafallopian device is described in *Transcatheter Tubal Sterilization in Rabbits*, Penny L. Ross, RT 29 "Investigative Radiology", pp. 570-573 (1994). The experimental use of an electrolytically pure copper wire as a surgical contraceptive intrafallopian device in rats was described in "Antifertility Effect of an Intrafallopian Tubal Copper Device", D.N. Gupta, 14 *Indian Journal of Experimental Biology*, pp. 316-319 (May 1976).

U.K. Patent Application Pub. No. 2,211,095 describes a uterine screw plug for blocking the fallopian tube. European Patent Application Pub. No. 0,010,812 describes a device for placement in the oviducts having enlargements at either end for anchoring the device. The same device appears to be described in Netherlands Patent No. 7,810,696.

The use of tubal occlusion devices is described in "Hysteroscopic Oviduct Blocking With Formed-in-Place Silicone Rubber Plugs", Robert A. Erb, Ph.D., et al., *The Journal of Reproductive Medicine*, pp. 65-68 (Aug. 1979). A formed-In-place elastomeric tubal occlusion device is described in U.S. Pat. No. 3,805,767, issued to Erb. U.S. Pat. No. 5,065,751, issued to Wolf, describes a method and apparatus for reversibly occluding a biological tube. U.S. Pat. No. 4,612,924, issued to Cimber, describes an intrauterine contraceptive device which seals the mouths of the fallopian tubes.

German Patent No. 28 03 685, issued to Brundin, describes a device for plugging a body duct with a device which swells when in contact with a body fluid.

Alternative contraceptive devices are disclosed in copending U.S. patent application Ser. No. 08/475,252, the full disclosure of which is herein incorporated by reference.

SUMMARY OF THE INVENTION

The present invention provides intrafallopian devices and methods for their placement to prevent conception. The intrafallopian devices of the present invention are transcervically delivered, resiliently anchored structures which are formed at least in part from copper to provide long term contraception, or alternatively permanent sterilization, without the need for surgical procedures or the increased bleeding, pain, and risks of infection associated with intrauterine devices (IUDs).

The use of copper in the intrafallopian device of the present invention improves its efficacy as a contraceptive method. Devices formed from plastically deformable materials, however, are less readily restrained in the fallopian tube. Apparently, the large variation in the actual shape and dimensions of fallopian tubes does not provide reliable anchoring for a pre-formed deformable intrafallopian device. The intrafallopian device of the present invention therefore comprises a resilient structure, usually a metallic coil, which includes a copper alloy, a copper plating, or copper fibers, ideally comprising an alloy including at least 75% copper. The coil material typically includes beryllium, zinc, stainless steel, platinum, a shape memory alloy such as Nitinol™, or the like. Preferably, the coil is composed of an alloy of beryllium and copper. Although the present device will generally result in occlusion, it need not completely occlude the fallopian tube to prevent the meeting of the sperm and ovum. Instead, the presence of the copper on the resilient structure is sufficient to provide effective contraception.

Conveniently, the present invention further comprises non-surgical placement of such intrafallopian devices by transcervical introduction. The resilient structure is restrainable in a straight configuration, e.g., by inserting the device within a catheter, greatly facilitating and reducing the risks of introduction. Thus, the cost and dangers associated with existing surgical contraceptive and sterilization procedures are avoided.

In a first aspect, a contraceptive intrafallopian device according to the present invention comprises a resilient structure having a proximal end and a distal end. The resilient structure comprises copper, and is biased to form at least one bend near the proximal end of the primary coil. Similarly, the resilient structure is also biased to form at least one bend near its distal end. These proximal and distal bends define an isthmus-traversing region therebetween. Preferably, the isthmus-traversing region also includes at least one bend, thereby helping to anchor the coil within the fallopian tube.

Generally, the resilient structure of the present intrafallopian device will be formed as a primary coil. To help restrain the coil within the fallopian tube, fibers are attached to some embodiments of the coil, the fibers optionally comprising a polyester material such as Rayon™, Dacron™, or the like. Alternatively, copper fibers may be used to increase the exposed copper surface area, the copper fibers generally having a diameter on the order of 0.001 inches.

The bends of the present intrafallopian device are generally formed as a secondary shape imposed on a primary coil. The primary coil is most easily formed as a straight cylindrical coil. The secondary shape will be imposed on the primary coil by bending, optionally heat treating the primary coil while bent. The individual bends may take a wide variety of forms, including sinusoidal curves, the individual loops of a continuous secondary coil, or the like. However, the secondary shape generally defines an overall width which is larger than the fallopian tube, so that the tubal wall restrains the resilient structure when it is released.

Preferably, each of the bends of the present intrafallopian device forms a loop in the primary coil when in a relaxed state. Ideally, the loops are separated by straight sections of coil. The alternating of loops with straight sections of coil forms a large diameter "flower coil," which provides a large relaxed overall width, and also features bends at tight radius, both of which promote retention. Conveniently, the primary coil generally has a diameter less than that of the fallopian tube, and can be restrained in a straight configuration for placement within the fallopian tube, typically by inserting the primary coil within a delivery catheter.

In another aspect, a contraceptive intrafallopian device according to the present invention comprises a resilient primary coil having a primary coil diameter. The primary coil comprises copper, and forms a secondary shape when in a relaxed state. The secondary shape defines a plurality of bends and an overall width which is larger than the primary coil diameter. Thus the primary coil can be easily anchored in a fallopian tube which is smaller in diameter than the secondary shape. Preferably, the present device reacts with a force sufficient to prevent axial movement of the device within the fallopian tube when restrained in a lumen having a diameter in the range between 0.5 mm and 3 mm. The actual anchoring force will depend on the shape of the coil and the modulus of elasticity of the material used.

In yet another aspect, a intrafallopian contraceptive delivery system according to the present invention comprises an elongate body in which the resilient primary coil described above is slidably disposed. A shaft is also slidably disposed within the elongate body and is located proximally of the primary coil. The distal end of the shaft includes a coil interface surface, while the elongate body restrains the primary coil in a straight configuration.

Preferably, a bend in the isthmus-traversing region of the present intrafallopian device, together with the proximal and distal anchor bends, restrains the resilient structure within the isthmus of the fallopian tube. The distal anchor is inserted into the ampulla, distal of the isthmus, while the proximal anchor is located in the ostium, proximal of the isthmus. Unintended movement of the device is further avoided by locating the isthmus-traversing region within the isthmus to resiliently impose anchoring forces against the tubal wall.

In a still further aspect, an intrafallopian contraceptive method according to the principles of the present invention comprises restraining a resilient structure in a straight configuration and transcervically inserting the resilient structure into a fallopian tube. The resilient structure is affixed within the isthmus by releasing a bent isthmus-traversing region. The bend of the isthmus-traversing region exerts a force against the wall of the fallopian tube, anchoring the device within the isthmus. Preferably, a distal anchor on the resilient structure is released distally of the isthmus, and a proximal anchor is released proximally of the isthmus, the distal and proximal anchors generally formed from bends in the resilient structure. Optionally, an electric current is applied through the resilient structure to the fallopian tube, thereby effecting permanent sterilization.

BRIEF DESCRIPTION OF THE DRAWINGS

FIG. 4 illustrates the contraceptive intrafallopian device of FIG. 1 partially released from the delivery catheter of FIG. 3.

FIGS. 5 and 6 illustrate a contraceptive method using an intrafallopian device according to the principles of the present invention.

DETAILED DESCRIPTION OF THE SPECIFIC EMBODIMENT

Figure 1:
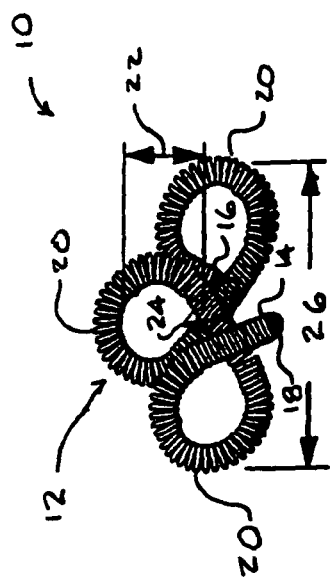
FIG. 1 illustrates a first embodiment of a contraceptive intrafallopian device according to the present invention having a single distal anchor loop, a single proximal anchor loop, and an isthmus-traversing region having a single loop for anchoring the device within the fallopian tube.

The present invention encompasses a contraceptive intrafallopian device which can alternatively be used as both a permanent and a reversible means of contraception. The present contraceptive methods and devices minimize the danger of non-use which has limited the efficacy of prior art contraceptive techniques. Moreover, the location of the present devices within the fallopian tubes provides a reduced risk of the infectious complications, increased bleeding, and pelvic pain associated with intrauterine devices (IUDs). Furthermore, the location and the novel shape of the present intrafallopian device provides significant advantages over IUDs, which have been found to be susceptible to unplanned expulsion and removal due to excessive pain and bleeding. The present invention takes advantage of the increase in effectiveness associated with copper IUDs, providing a resilient structure including copper which may be transcervically positioned without the need for surgery.

Although the present contraceptive method may be included within a group of contraceptive techniques generally referred to as fallopian tube occlusion methods, the present invention does not necessarily rely solely on blocking the fallopian tube to prevent fertilization. Instead, contraception is apparently provided by disrupting of ovum transport, the process of fertilization, and/or cleavage of the ovum. While the effect that copper has on these processes is not fully understood, it does appear that copper intrafallopian devices offer potentially significant increases in effectiveness over intrafallopian devices formed of other materials. Optionally, the present invention further encompasses devices which promote tissue growth within the tube to induce tubal occlusion, further inhibiting conception.

The present invention is anchored within the isthmus of the fallopian tube, overcoming the unintended expulsion of the device and the resulting failure of the contraceptive method. Such intrafallopian device expulsion has been the single greatest factor limiting the efficacy of easily positioned intrafallopian contraceptive techniques.

The present intrafallopian devices are generally elongate resilient structures preformed into secondary shapes. These secondary shapes will bias the resilient structure so as to provide strong forces against the lumen wall of the fallopian tube. Clearly, the secondary shape must have a larger outer diameter than the inner diameter of the fallopian tube.

Conveniently, the present resilient structures are insertable into a catheter, the catheter wall restraining the resilient structure in a straight configuration. As the resilient structure has an outer diameter when in the straight configuration which is less than the inner diameter of the fallopian tube, the catheter containing the present intrafallopian device is easily transcervically introduced. Moreover, the device is readily removed by snaring the resilient structure near the proximal end and pulling proximally on the resilient structure, thereby straightening the resilient structure and allowing it to be withdrawn without injuring the fallopian tube. Alternatively, an electrical current is applied to the device after it is at least partially releasing the fallopian tube, providing permanent sterilization.

Referring now to FIG. 1, a first embodiment of the present contraceptive intrafallopian device 10 is formed from a resilient primary coil 12. Primary coil 12 is most easily originally formed as a straight cylindrical coil or spring, preferably having an outer diameter in the range from 0.2 mm to 5 mm, and having a length in the range from 20 mm to 150 mm. Ideally, primary coil 12 has an outer diameter in the range from 0.4 DUD to 2 mm and a length in the range from 30 mm to 70 mm. The straight primary coil may then be bent into a variety of secondary shapes.

The primary coil 12 of intrafallopian device 10 includes a proximal end 14 and a distal end 16. Between these ends, three loops 20 are formed, each having an inner diameter 22. Located between loops 20 are straight sections 24, which increase the overall cross-section of the intrafallopian device to an overall width 26. Preferably, inner diameter 22 is in the range from 2 mm to 10 mm, while overall width 26 is at least 6 mm, ideally being in the range from 8 mm to 40 mm. Distal and proximal ends 14, 16 each include an atraumatic endcap 18 to prevent injury to the fallopian tube.

Preferably, primary coil 12 is formed from a beryllium copper alloy wire. Beryllium copper provides the resilience necessary to avoid expulsion of the device, and also provides the increased effectiveness of a copper contraceptive intrafallopian device. Alternatively, primary coil 12 is formed from a resilient metal, such as stainless steel, platinum, a shape memory alloy, or the like. If such materials are used, primary coil 12 is preferably plated with copper or a copper alloy or otherwise has copper attached.

To further reduce the possibility of expulsion of intrafallopian device 10, fibers are optionally carried on primary coil 12. The fibers may be short individual fibers, or may alternatively be wound into primary coil 12. Preferably, the fibers comprise copper, thereby increasing the total copper surface area. Such copper fibers are preferably bonded to primary coil 12 with solder, brazing, a polymeric adhesive, or the like. Alternatively, polyester fibers such as Dacron™, Rayon™, or the like, are bonded to the surface of primary coil 12 using a polymeric adhesive. The polyester fibers promote increased tissue growth around the coil, thus further reducing the possibility of expulsion of the device from the fallopian tube.

A secondary shape has been superimposed on the primary coil to form intrafallopian device 10, the secondary shape comprising loops 20 separated by straight sections 24. This secondary shape is herein referred to as a "flower coil." The flower coil shape is particularly advantageous in that outer diameter 26 is substantially larger than the primary coil diameter, while the individual loops 20 have relatively small inner diameters 22 which will maintain the largest possible anchoring force against the fallopian tube. Minimizing inner diameter 22 also ensures that anchoring force is applied within the fallopian tube, despite the curvature of the fallopian tube.

Figure 2:
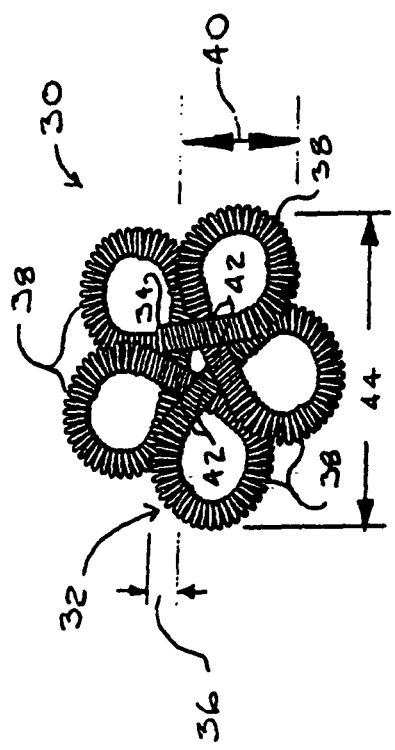
FIG. 2 illustrates an alternative embodiment of a contraceptive intrafallopian device according to the present invention having a plurality of loops which may act as proximal, distal, or lumen anchors.

Referring now to FIG. 2, an alternative embodiment of the present contraceptive intrafallopian device 30 includes additional loops to ensure anchoring of the device within the fallopian tube. Alternative embodiment 30 is formed from an elongate primary coil 32 having a proximal end 34 and a distal end (not shown). Elongate primary coil 32 has an outer diameter 36 which is smaller than the isthmus of the fallopian tube, allowing the straightened intrafallopian device to be inserted easily. Elongate primary coil 32 has been bent to form a secondary shape including a larger number of loops 38 than the embodiment of FIG. 1. Loops 38 have an outer diameter 40 which is larger than the inner diameter of the fallopian tube, preventing loops 38 from assuming their relaxed shape. Loops 38 are again separated by straight sections 42 of elongate primary coil 32, increasing the overall intrafallopian device diameter 44.

In both embodiments of the present intrafallopian device 10, 30, at least one loop adjacent to the proximal end is disposed proximally of the narrowest portion of the fallopian tube, referred to as the isthmus. Similarly, at least one loop of the intrafallopian device is disposed distally of the isthmus. These proximal and distal loops act as anchors, helping to prevent proximal or distal movement of the intrafallopian device. In the embodiment of FIG. 2, at least one loop is also disposed adjacent to the isthmus of the fallopian tube, further helping to prevent unintentional expulsion.

Alternative intrafallopian device 30 may be positioned with multiple loops acting as proximal or distal anchors, or may alternatively have all but the proximal and distal anchor loops disposed along the fallopian tube to act as anchors within the lumen of that body. Advantageously, the embodiment of FIG. 2 is therefore less sensitive to variations in total fallopian tube length.

Figure 3:
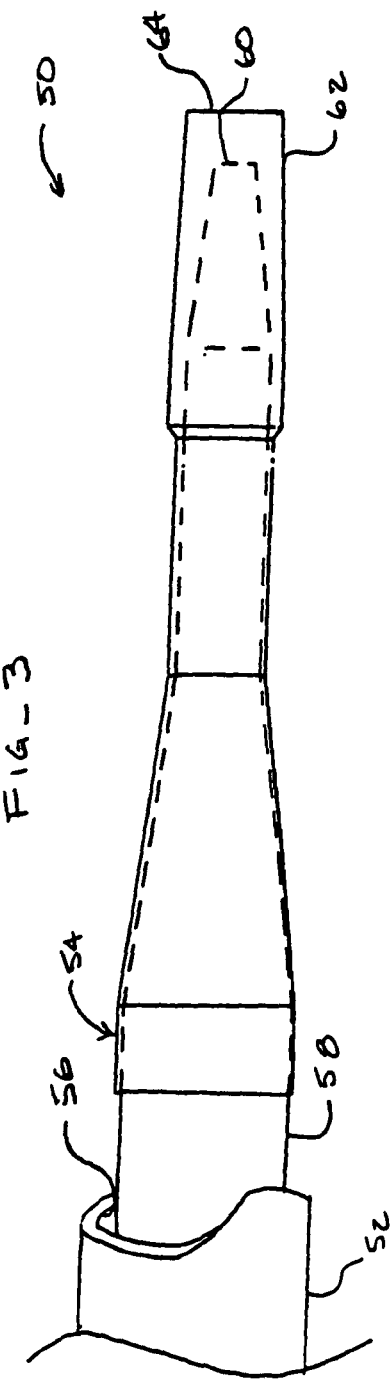
FIG. 3 illustrates the distal portion of a delivery catheter for placement of a contraceptive intrafallopian device according to the present invention.

Referring now to FIG. 3, a delivery catheter for the present intrafallopian device comprises an elongate body 52 and a shaft 54. Elongate body 52 includes a lumen .56 in which shaft 54 is disposed, shaft 54 being slidable in the axial direction. Shaft 54 includes a core 58 having a tapered distal end 60, allowing the device to navigate through tortuous bends while retaining the column strength required to advance the device. Core 58 extends proximally through elongate body 52, and is capable of transferring compressive forces through the elongate body. Core 58 is typically formed from stainless steel, a stainless alloy, or the like. Disposed over distal end 60 of core 58 is pusher cap 62. Pusher cap 62 provides a low friction, deformable end piece having a distal coil interface surface 64. Pusher Cap 62 is preferably formed of a low friction polymer such as PTFE, or the like.

Intrafallopian delivery catheter 50 receives the present intrafallopian device within the distal end of lumen 56 of elongate body 52. Lumen 56 has an inner diameter which is slightly larger than outer diameter 36 of the primary coil. The present intrafallopian device is therefore straightened to a straight configuration as it is loaded proximally into the distal end of lumen 56. Elongate body 52 is sufficiently strong to restrain the primary coil in the straight configuration, but must remain sufficiently flexible to allow maneuvering within the body lumen. Elongate body 52 is preferably formed from an inelastic, flexible material such as polyurethane, PET, or the like.

Referring now to FIG. 4, intrafallopian device 10 is released from delivery catheter 50 within the fallopian tube by holding shaft 54 while proximally withdrawing elongate body 52. Distal coil interface surface 64 engages the proximal end 14 of primary coil 12. Initially, primary coil 12 is restrained in a straight configuration by elongate body 52. As elongate body 52 is withdrawn, primary coil 12 is released. When primary coil 12 is unrestrained it forms loop 20; when released within the fallopian tube it will generally be restrained by the tubal wall in a configuration between straight and the relaxed secondary shape. Preferably, the first loop released will form a distal anchor bend 66. Subsequent loops will bias primary coil 12 against the fallopian tube, and form a proximal anchor bend, in that order.

Use of the present contraceptive intrafallopian device will be described with reference to FIGS. 5 and 6. A uterine introducer canula 70 is inserted transcervically through a uterus 72 to the region of an ostium 74. Elongate body 52 is then extended distally from canula 70 into a fallopian tube 77, preferably guided under fluoroscopy. Alternatively, a hysteroscope may be used in place of canula 70. Elongate body 52 is maneuvered using a guide wire 78 past an isthmus 80.

After elongate body 52 extends past isthmus 80, guide wire 78 is removed. An intrafallopian device according to the present invention is inserted in the proximal end of elongate body 52, the intrafallopian device being restrained in a straight configuration by the elongate body. The device is advanced distally using shaft 54, the shaft and elongate body forming delivery catheter 50 (FIG. 3). Delivery catheter 50 is axially positioned so that at least one loop of the intrafallopian device is within a target region 84 adjacent to isthmus 80. Preferably, at least one loop is distal of target region 84, and at least one loop is proximal of target region 84 to form the distal and proximal anchor bends of the implanted intrafallopian device.

Once delivery catheter 50 is properly positioned, elongate body 52 may be axially withdrawn. Shaft 54 axially restrains the intrafallopian device at the target location during withdrawal of elongate body 52, as described regarding FIG. 4. As the distal end at the primary coil is released, the distal loop forms a distal anchor bend 90. Similarly, the proximal loop forms a proximal anchor bend 92. Intermediate loops are restrained within the narrow target region 84, exerting substantial anchoring forces against the walls of the fallopian tube. As seen in FIG. 6, the loops need not assume their relaxed form to provide effective distal or proximal anchors.

The present invention further encompasses permanent sterilization by passing a current through the shaft to the intrafallopian device after elongate body 52 has been partially withdrawn, but before the intrafallopian device is fully released. Fallopian tube tissue in contact with the intrafallopian device is desschated, and thus attached to the present intrafallopian device. This action also causes permanent tubal damage, leading to the formation of scar tissue which encapsulates the intrafallopian device and causes permanent occlusion of the tubal lumen. Clearly, the resilient member/shaft interface must be conductive to allow the present non-surgical method of permanent sterilization.

In conclusion, the present invention provides a contraceptive intrafallopian device which may be positioned without surgery. While the above is a complete description of the preferred embodiments of the invention, various alternatives, modifications, and equivalents may be used. For example, a wide variety of secondary shapes, including open loops, continuous bends, sinusoidal curves, or the like, may be imposed on the primary coil. Therefore, the above description should not be taken as limiting the scope of the invention, which is defined instead solely by the appended claims.

What is claimed is:

1. A female contraceptive method comprising:
    delivering a first expandable anchor to a first location of a female reproductive organ, the first expandable anchor being radially restrained before being delivered, the first expandable anchor being delivered through a shaft which is transcervically introduced;
    delivering a second expandable anchor to a second location of a female reproductive organ, the second expandable anchor being radially restrained before being delivered, the second expandable anchor being adjacent a straight section of a contraceptive device after being delivered, wherein the straight section comprises a substantial portion of the contraceptive device; and
    performing an operation with the shaft after the delivery of the first expandable anchor but before the delivery of the second expandable anchor.

2. A method as in claim 1 wherein the operation comprises delivering a current through the shaft.

3. A method as in claim 1 wherein the first expandable anchor expands at the first location and the second expandable anchor expands at a second location after the first expandable anchor expands.

4. The method as in claim 1, wherein the first expandable anchor comprises an agent to cause tissue growth and the second expandable anchor comprises an agent to cause tissue growth.

5. The method as in claim 1, wherein the first expandable anchor comprises a first resilient structure and the second expandable anchor comprises a second resilient structure.

6. A device comprising:
    a delivery shaft configured to be transcervically introduced into a female reproductive organ;
    a first expandable anchor coupled to the delivery shaft;
    a second expandable anchor coupled to the delivery shaft, the first expandable anchor being radially restrained before being delivered by the delivery shaft and the second expandable anchor being radially restrained before being delivered by the delivery shaft, the second expandable anchor being adjacent a straight section of a contraceptive device after being delivered, wherein the straight section comprises a substantial portion of the contraceptive device after being delivered, and wherein the delivery shaft is configured to perform an operation after delivering the expandable anchor and before delivering the second expandable anchor.

7. A device as in claim 6 wherein the first expandable anchor expands at a first location and the second expandable anchor expands at a second location after the first expandable anchor expands.

8. A device as in claim 7 wherein the first expandable anchor and the second expandable anchor each comprise a pre-formed resilient structure which is adapted to resiliently engage a surrounding wall of a fallopian tube.

9. A device as in claim 8 further comprising fibers coupled to each of the first expandable anchor and the second expandable anchor, the fibers promoting tissue growth in a fallopian tube.

10. The device as in claim 6, wherein the first expandable anchor comprises an agent to cause tissue growth and the second expandable anchor comprises an agent to cause tissue growth.

11. The device as in claim 6, wherein the first expandable anchor comprises a first resilient structure and the second expandable anchor comprises a second resilient structure.

12. A device comprising:
a delivery shaft configured to be transcervically introduced into a female reproductive organ;
a first expandable anchor disposed on the delivery shaft;
a second expandable anchor disposed on the delivery shaft, the first expandable anchor being radially restrained before being delivered by the delivery shaft and the second expandable anchor being radially restrained before being delivered by the delivery shaft, the second expandable anchor being adjacent a straight section of a contraceptive device after being delivered, wherein the straight section comprises a substantial portion of the contraceptive device after being delivered, and wherein the delivery shaft is configured to perform an operation after delivering the first expandable anchor and before delivering the second expandable anchor.

13. A device as in claim 12 wherein the first expandable anchor expands at a first location and the second expandable anchor expands at a second location after the first expandable anchor expands.

14. A device as in claim 13 wherein the first expandable anchor and the second expandable anchor each comprise a pre-formed resilient structure which is adapted to resiliently engage a surrounding wall of a fallopian tube.

15. A device as in claim 14 further comprising: fibers coupled to each of the first expandable anchor and the second expandable anchor, the fiber promoting tissue growth in a fallopian tube.

16. The device as in claim 12, wherein the first expandable anchor comprises an agent to cause tissue growth and the second expandable anchor comprises an agent to cause tissue growth.

17. The device as in claim 12, wherein the first expandable anchor comprises a first resilient structure and the second expandable anchor comprises a second resilient structure.

18. A device comprising:
a delivery shaft configured to be transcervically introduced into a female reproductive organ;
a first expandable element designed to prevent axial movement coupled to the delivery shaft;
a second expandable element designed to prevent axial movement coupled to the delivery shaft, the first expandable element being radially restrained before being delivered by the delivery shaft and the second expandable element being radially restrained before being delivered by the delivery shaft, the second expandable element being adjacent a straight section of a contraceptive device after being delivered, wherein the straight section comprises a substantial portion of the contraceptive device after being delivered, and wherein the delivery shaft is configured to perform an operation after delivering the first expandable element and before delivering the second expandable element.

19. A device as in claim 18 wherein the first expandable element expands at a first location and the second expandable element expands at a second location after the first expandable element expands.

20. A device as in claim 19 wherein the first expandable element and the second expandable element each comprise a pre-formed resilient structure which is adapted to resiliently engage a surrounding wall of a fallopian tube.

21. A device as in claim 20 further comprising: fibers coupled to each of the first expandable element and the second expandable element, the fiber promoting tissue growth in a fallopian tube.

22. The device as in claim 18, wherein the first expandable anchor comprises an agent to cause tissue growth and the second expandable anchor comprises an agent to cause tissue growth.

23. The device as in claim 18, wherein the first expandable anchor comprises a first resilient structure and the second expandable anchor comprises a second resilient structure.

24. A device comprising:
a longitudinally disposed member having a distal portion and a proximal portion;
a first expandable anchor coupled to the longitudinally disposed member near the distal portion, the first expandable anchor being radially restrained before being delivered to a fallopian tube;
a second expandable anchor coupled to the longitudinally disposed member near the proximal portion, the second expandable anchor being radially restrained before being delivered to a fallopian tube, the second expandable anchor being adjacent a straight section of a contraceptive device after being delivered, wherein the straight section comprises a substantial portion of the contraceptive device after being delivered;
a delivery shaft coupled to the longitudinally disposed member, the delivery shaft being adapted to introduce the longitudinally disposed member into the fallopian tube and to detach from the longitudinally disposed member to leave the longitudinally disposed member within the fallopian tube.

25. A device as in claim 24 wherein the first expandable anchor expands at a first location after being delivered and the second expandable anchor expands at a second location after being delivered and wherein the first expandable anchor expands before the second expandable anchor expands.

26. A device as in claim 24 wherein the first expandable anchor and the second expandable anchor each comprise a preformed resilient structure which is adapted to resiliently engage a surrounding wall of the fallopian tube.

27. A device as in claim 26 further comprising fibers coupled to the female contraceptive device.

28. The device as in claim 24, wherein the first expandable anchor comprises an agent to cause tissue growth and the second expandable anchor comprises an agent to cause tissue growth.

29. The device as in claim 24, wherein the first expandable anchor comprises a first resilient structure and the second expandable anchor comprises a second resilient structure.

* * * * *